(12) United States Patent
Larsen

(10) Patent No.: US 7,033,381 B1
(45) Date of Patent: Apr. 25, 2006

(54) PHOTODYNAMIC STIMULATION DEVICE AND METHOD

(76) Inventor: Erik Larsen, P. Fach 1016, 8201 Schaffhausen (CH)

(*) Notice: Subject to any disclaimer, the term of this patent is extended or adjusted under 35 U.S.C. 154(b) by 606 days.

(21) Appl. No.: 09/711,462

(22) Filed: Nov. 13, 2000

Related U.S. Application Data

(63) Continuation-in-part of application No. 08/094,161, filed as application No. PCT/CH92/00228 on Nov. 20, 1992, now abandoned.

(30) Foreign Application Priority Data

Nov. 20, 1991 (CH) ..................................... 3398/91

(51) Int. Cl.
*A61F 7/00* (2006.01)
(52) U.S. Cl. .......................................... 607/88; 607/90
(58) Field of Classification Search ............. 607/88–92
See application file for complete search history.

(56) References Cited

U.S. PATENT DOCUMENTS

| | | | | |
|---|---|---|---|---|
| 4,614,190 A | * | 9/1986 | Stanco et al. ................... | 607/88 |
| 4,930,504 A | * | 6/1990 | Diamantopoulos et al. ... | 607/88 |
| 5,077,588 A | * | 12/1991 | Yamada et al. ................ | 257/96 |
| 5,095,901 A | * | 3/1992 | Davitashvili et al. .......... | 607/88 |
| 5,138,624 A | * | 8/1992 | Hong et al. ................... | 372/45 |
| 5,262,401 A | * | 11/1993 | Vogel et al. ................... | 514/32 |
| 6,096,066 A | * | 8/2000 | Chen et al. ................... | 607/88 |
| 6,231,593 B1 | * | 5/2001 | Meserol ........................ | 607/88 |
| 6,443,976 B1 | * | 9/2002 | Flower et al. ................ | 607/88 |

\* cited by examiner

Primary Examiner—Robert L. Nasser
(74) Attorney, Agent, or Firm—Cohen, Pontani, Lieberman & Pavane

(57) ABSTRACT

A treatment device which uses cold red and infrared radiation for the photodynamic stimulation of cells, especially cells of human tissue. The described device produces a constant energy radiation by the use of semiconductor and/or laser diodes, which furthermore radiate light in several separate wavelengths due to a special operation mode. With help of sensors the advanced controller system is able to test the patients for the needed radiation doses in order to avoid overstimulation. Furthermore the radiation openings in the applicators are advantageously covered with a polarization filter, whereby the absorption in the irradiated tissue is increased. The basic equipment consists of a standpillar, with which machine applicators are connected with a jointed arm. The machine applicators are adapted for the treatment of large area tissues, for example, the back of humans. The standpillar is freely movable on wheels and includes a control mechanism, whereby the various parameters for therapy can be adjusted and switched ON and OFF. The standpillar is also connected to a hand applicator designed for the treatment of small tissue areas, e.g., acupuncture points. Another version of the hand applicator is especially devised for dental treatment, whereby the head piece of the hand applicator can be connected with an expander containing an optical fiber. Photodynamic substances are introduced into tissue to be treated, which enhances the effects of light irradiation by the inventive device.

56 Claims, 3 Drawing Sheets

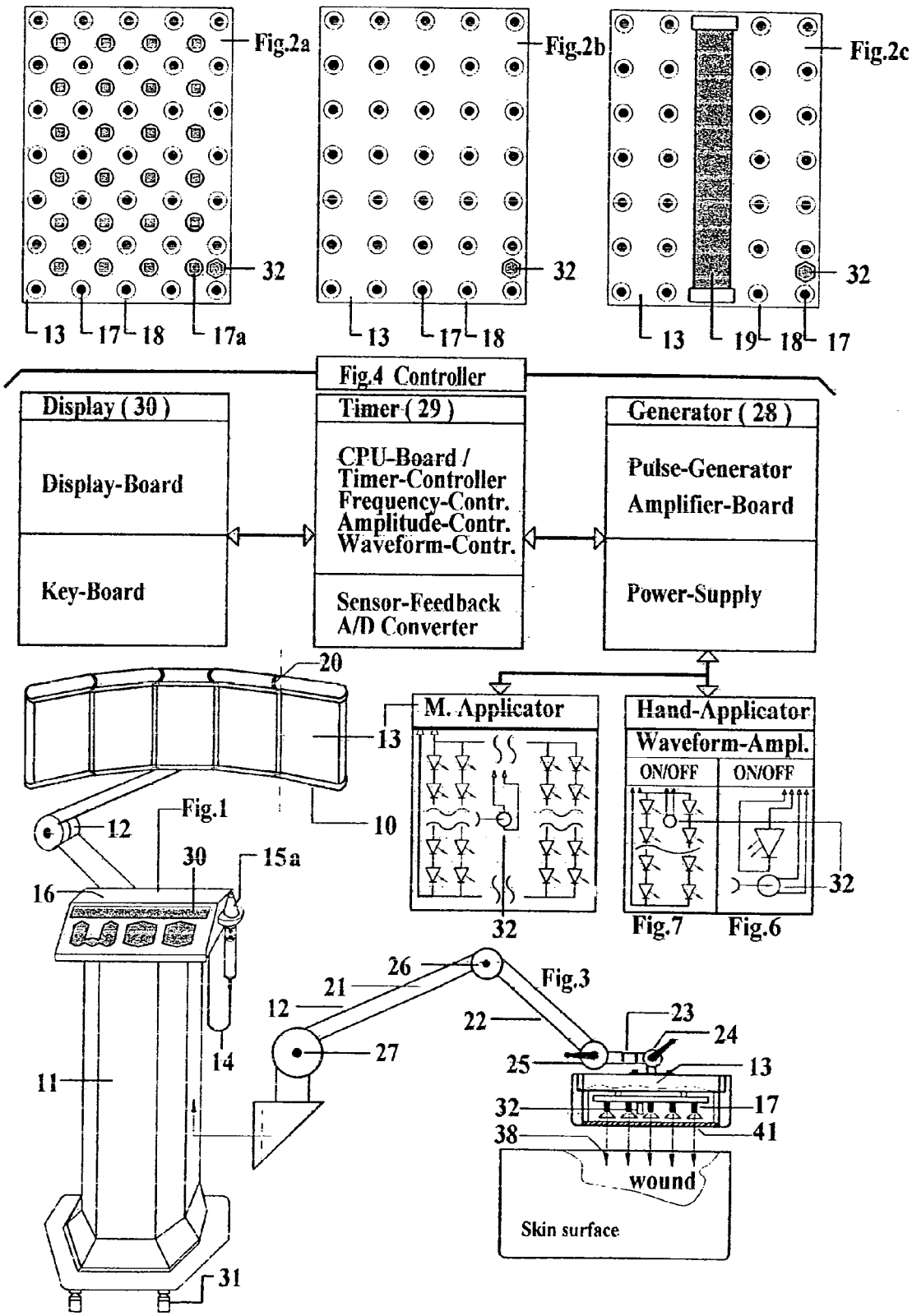

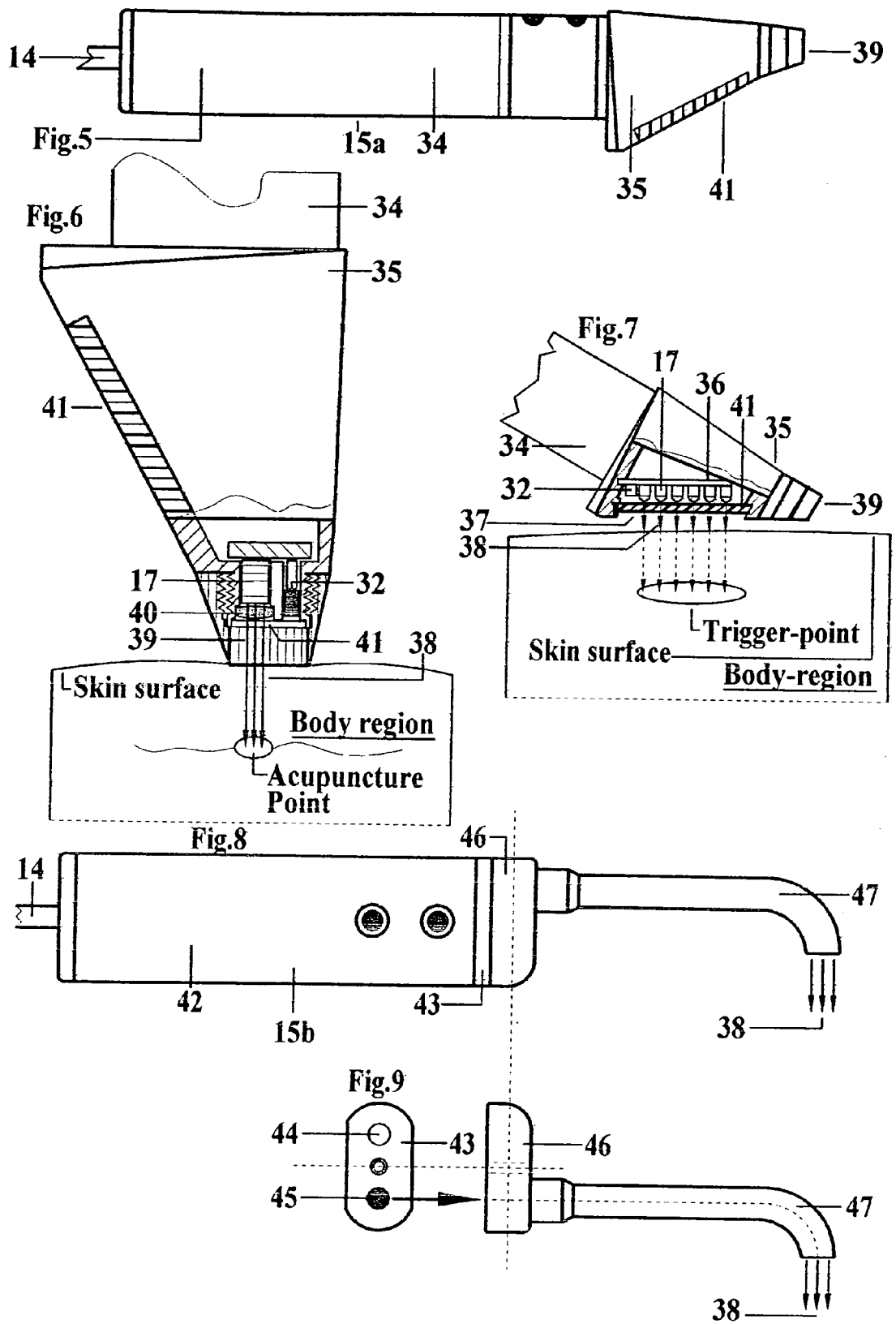

PHOTODYNAMIC STIMULATION DEVICE AND METHOD

CROSS-REFERENCE TO RELATED APPLICATIONS

This application is a continuation-in-part of U.S. application Ser. No. 08/094,161 filed Dec. 20, 1993, now abandoned, which is a national stage of PCT Application No. PCT/CH92/00228 filed Nov. 20, 1992. The entire contents of both applications are incorporated by reference.

BACKGROUND OF THE INVENTION

1. Field of the Invention

The present invention relates in general to electrotherapy devices and more particularly to devices and methods for photodynamic stimulation of living tissue, directly and also indirectly by stimulation of photosensitive substances introduced into or onto living tissue.

2. Description of the Related Art

Mitochondria within cells of protozoa and metazoa represent sources of energy delivering vesicular respiration. They are moreover capable of synthesizing proteins, because they dispose from the cell nucleus an independent or self-dependent genetic system of DNA and RNA.

The mitochondria's main function however is vesicular respiration, that is within the cells the transformation of nutrient media and oxygen either supplied through the blood stream or in some other way into energy and endogenous substances, whereby through this transformation, waste products like water, carbon dioxide, alcohol and lactic acid are produced. Of great importance is adenosine-triphosphorus acid (ATP), which is synthesized by the mitochondria into adenosine-diphosphorus acid (ADP) and orthophosphate. Complicated chemical compounds are of great importance as reaction catalyst.

Stimulation of the vesicular respiration, especially a stimulation of the ATP production by cells, is used therapeutically, preferably for the promotion of strong use of cell energy in the healing processes and by reduction of weight, healing of wounds and a reduction of pain sensitivity due to an illness or weakness caused by hypopolarization or depolarization of the cell membrane. In general, weakening of cells caused by an increase of vesicular respiration due to stress, illness or by old age can be counteracted. In order to achieve stimulation of the mitochondria through optical radiation, two conditions must be fulfilled. The radiation must be of appropriate wavelengths in order to be effective, and a pulse frequency must be chosen to penetrate to an appropriate tissue depth without causing tissue damage or pain.

A device is known (Patent DE-U-8813852/Normed, E. Larsen). which uses infrared radiation for the photodynamic stimulation of energy in living cells, cells at the surface of the skin and especially cells lying deeper down. The device consists of a supply and control mechanism and an applicator on which infrared radiation from 900 nm (1 nm=1 nanometer) radiating IR (infrared) semiconductor diodes are mounted with reflectors for the bundling of the IR radiation from the applicator. In this known device, a generator containing a controller mechanism supplies the semiconductor diodes with current pulses of a certain frequency within the range of 500–5000 Hz. A disadvantage of the known device is that the semiconductor diodes during use tend to overheat, which causes a decrease in the effectiveness of the device. The known device therefore does not deliver a constant effect during use. Another disadvantage is that only infrared radiation within a range of 900 nm is available, while other wavelengths may be called for to achieve cell stimulation.

Light is used for bonding and hardening of plastic composite filling materials containing an agent which is photosensitive to light of 400–500 nm. wavelength (blue light). Worldwide, there are many producers of such materials (e.g., 3M Corporation, which also manufactures appropriate lamps). Information on these materials and lamps may be found on the Internet.

Well known in the art is a halogen lamp with a lamp housing including a reflector and a filter to obtain light output in the 400–500 nm. range (blue light). The housing also contains a fan to cool the lamp and filter but practical considerations concerning the size of the housing and the capacity of the fan typically result in insufficient cooling during operation, which causes the light output to vary. This can result in improper hardening, and perhaps also shrinking, of the fillings. Further, the lamps and filters must be replaced frequently. And, the apparatus is bulky and thus unwieldy in use.

The halogen apparatus has in the past been used mainly for setting plastic fillings in front teeth where relatively small amounts of filling material are used, and access is relatively easy. Recently however, there has been speculation that so-called silver fillings (actually mercury based) which have traditionally been used in the larger teeth may pose health risks, and many patients are requesting plastic fillings instead. Fillings in the larger teeth require much more filling material, and thus much more light dosage in order to harden properly without shrinkage, than in front teeth. The difficulties of using the unwieldy halogen apparatus are thereby exacerbated. For example, operating them at higher output results in temperature fluctuation, which in turn results in fluctuation of the light intensity which may result in improper hardening, and perhaps even shrinkage, of the fillings. Also, the lamps will have to be replaced more often.

In the field of dermatology, light is used as a stand-alone therapy for wounds, leg ulcers, eczema, burns, etc., and as such is used to stimulate tissue directly. Techniques are known for introducing agents for altering the light absorbing qualities of tissue to enhance the effect of light (for example, U.S. Pat. No. 5,226,907 to Tankovich teaches contamination of hair follicles with a dark particulate material to enhance light-induced heating in the follicles for hair removal).

Treatments have included the application of substances such as photofrin, 5-aminolevulan acid, hematoporphyrin, verteporfin, chlorins, phthalodyanines, phenothiazine, and benzoporphyrin-derivative monoacid-A (ATMPn) onto or into tissue for healing solar keratoses, basal cell carcinoma, melanomas, etc. Such substances are known as "biopharmaceuticals" and treatment with these substances has been called biopharmaceutical therapy. Therapy involving the application of biopharmaceuticals and their subsequent activation by light after they have been absorbed into tissue has been called photodynamic therapy (PDT).

PDT has been used successfully in the treatment of internal inoperable cancers. A biopharmaceutical (specifically, hematoporphyrin) is injected into the tumor tissue, and an optical method known as photodynamic diagnostic (PDD) is used to determine when the biopharmaceutical has been absorbed by the entire tumor. Then the tumor tissue is irradiated with light typical for a dye laser, which activates the photosensitive reactors in the hermatoporphyrin, whereby singlet oxygen is liberated. Singlet oxygen is toxic to protein and phosphorlipids in the tumor tissue, whereby the tumor is destroyed without destroying the surrounding tissue.

For treatment of skin keratosis (pre-cancerous tissue), trials with, for example, 5-aminolevulinic acid have shown that it can be used effectively in PDT if introduced into oil in a water suspension which is then applied to skin keratosis and then irradiated with a light source. A fast and cosmetically perfect healing has been attained with a very low rate of recurrence compared to conventional treatments, such as cryotherapy.

In view of these favorable test results, it is anticipated that pharmaceutical companies will be marketing the next generations of PDT chemicals in convenient forms, such as creams, suspensions, sprays, etc.

The light source typically used to irradiate PDT chemicals is commonly known as the surgical laser, a solid-state laser which is bulky, and which is expensive both to purchase and to operate. Surgical lasers are designed primarily for cutting, i.e., they output very high energy in a very small spot, and are thus difficult to adapt to the requirement to irradiate a more generalized area for PDT. Further, they generally radiate at a single wavelength. Radiation at several wavelengths is desirable in PDT, for several reasons: a single wavelength may cause the patient to experience burning pain in the tissue adjoining the tissue under treatment; some photosensitive chemicals respond to two different wavelengths; and, some pigmented melanomas do not respond to visible radiation due to absorption in the pigment (typically melanin), and must be irradiated with near-infrared light.

Common dermatological diseases like acne, warts, and onychomycosis (nail fungus) can successfully be treated with light as a stand-alone treatment, but recent work indicates that treatments using PDT (with ALA/5-aminolevulanic acid) give excellent results with only two or three treatments.

In a recent pilot study using PDT to treat acne, the cosmetic results were excellent, and oil gland activity which causes acne, and the resultant inflammation, were reduced for as much as twenty weeks after a series of PDT treatments. (The PDT treatments precipitated immediate but short-term inflammatory reactions.) In general the photodynamic stimulation used in the physiotherapy is producing very good results, but in the area of long-term chronic diseases such as gout, arthritis, etc. there is often a need for many treatments, as many as 12–20 treatments spaced over a period of time. Also, initial phases of such treatment often cause reactions, which in turn cause pain and discomfort.

SUMMARY OF THE INVENTION

The present invention provides a device using red and infrared radiation of several wavelength ranges suited for the photodynamic stimulation of the cell energy in living cells, in particular human cells of both surface and underlying tissue. Furthermore, blue light is provided as well to enhance vesicular respiration, particularly stimulation of the ATP production in cells, thus enhancing the therapeutic capabilities of the device.

The device consists of a standpillar, with which machine applicators are connected through a jointed arm. The standpillar, freely moveable on wheels, consists of control mechanism, whereby the desired therapy data can be adjusted and the device can be switched ON and OFF. The plain surface applicators can consist of more applicators placed side by side, connected and moveable with each other through hinges, whereby the applicators are suitable for the treatment of large-area tissues, for example, the human back.

The applicators contain printed circuit boards mounted with semiconductor diodes and/or laser diodes (in large numbers) and the diodes are mounted with reflectors, which collect the radiation and bundle them in front of the applicator. At least one of the applicator elements is equipped with sensors for controlling if the amount of radiation is suitable for the patient. The applicator contains a polarization filter, which is placed directly in front of the diodes. The control mechanism is also connected with a hand applicator. which is constructed for treatment of small tissue areas, e.g., acupuncture points and trigger points (pain points). The hand applicator includes a cylindrical shaft, to which a headpiece is connected. At the head piece a printed circuit board is fastened mounted with semiconductor diodes or laser diodes. The light radiation emits from a cleft in the head piece, which also has a light radiation opening in the front. In the head piece, in front of the opening, a lens for the focusing of the light rays and a polarization filter is placed. A second version hand applicator, which is especially invented for dental treatment shows at the front end of the shaft a printed circuit board, where an IR(infrared) light semiconductor diode or laser diode and a blue light semiconductor diode are placed. The head piece in front of the printed circuit board can be rotated 180 o so that the expander, which contains an optical fiber, can be positioned in front of either the one or the other radiation source.

The invention provides multiple wavelength stimulation that is effective in conjunction with photodynamic therapy (PDT) chemicals. Such chemicals are applied or injected into or onto tissue to be treated, and subsequent photostimulation of them causes reactions in them that result in treating the tissue. Irradiation at multiple wavelengths enhances the effects of PDT chemicals while reducing discomfort to the patient.

The present invention provides an apparatus including a semiconductor light source, and further includes a hand applicator. The applicator may selectively emit blue light for the bonding and hardening of composite plastic fillings or infrared light for treatment of dental pain, gingivitis, and wounds. In order to optimize bonding by the blue light, output of the hand applicator is supplied at 25% of full power for the first ten seconds of the radiation time, and then is switched to full power.

Other advantages of the invention will become evident from the following description of the invention and from the appended drawings, wherein:

BRIEF DESCRIPTION OF THE DRAWINGS

FIG. 1 is a drawing of the inventive device in perspective description;

FIGS. 2a, 2b, 2c illustrate details from the machine applicator of the inventive device;

FIG. 3 illustrates a jointed arm used for the movable connection of the machine applicators;

FIG. 4 is a circuit block diagram of a controller unit, which supplies the applicators.

FIG. 5 depicts a hand applicator according to the present invention;

FIG. 6 depicts an applicator conforming to FIG. 5 with axial light emission;

FIG. 7 depicts an applicator conforming to FIG. 5 with radial light emission;

FIG. 8 an applicator with a rotary headpiece;

FIG. 9. shows details of a printed circuit board for the applicator of FIG. 8.

DETAILED DESCRIPTION OF THE PREFERRED EMBODIMENT

Figure 10:
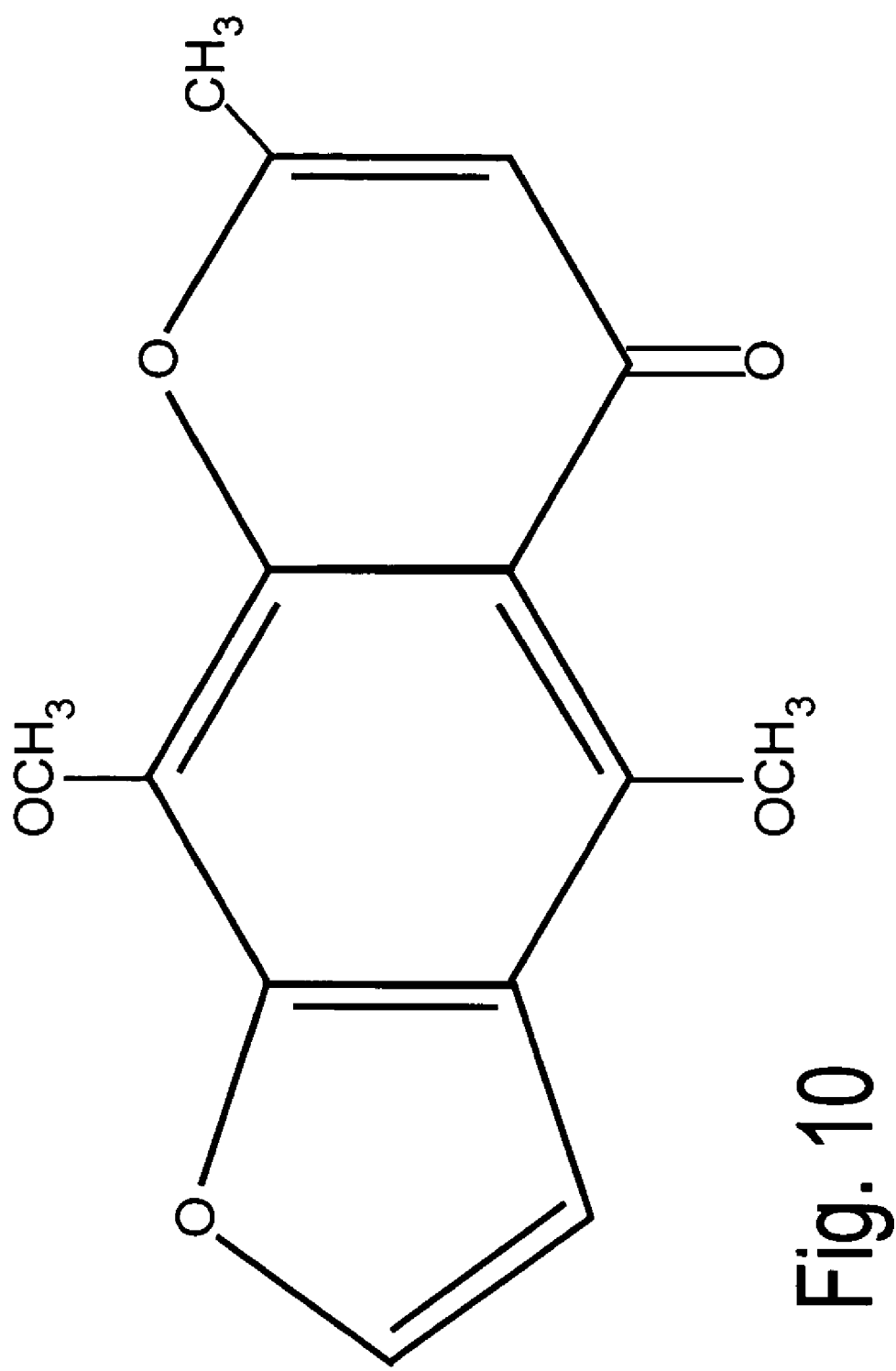
FIG. 10 depicts the molecular structure of ammi visnaga, a herbal substance for use with the present invention.

As shown in FIG. 1, the inventive device 10 for the energy stimulation of cells consists of a standpillar 11, with which machine applicators 13 (in the following just called applicators 13) are connected through a jointed arm 12. The standpillar 11 is also connected by an electric circuit 14 with hand applicator 15. The standpillar 11, freely movable on wheels, includes control mechanism 16 (described in FIG. 4). whereby the function of the control mechanism 16 can be adjusted and switched ON/OFF at a control board 30 (also called description equipment 30).

The FIGS. 2a, 2b and 2c show plain surfaced applicators 13. which can be used in the working model according to FIGS. 2a to 2c individually, side by side (in large numbers) or in combination with an applicator. According to FIG. 2 a, the applicators 13 in the working model are mounted in a shifting order with semiconductor diodes 17 and 17a (in the following called diodes), whereby shifting the order of diodes 17 means, that the respective diode 17a of one row is placed at the point of intersection of the two diagonals through the two respective diodes 17, which are placed adjoining on both sides. The diodes 17 and 17a are mounted with reflectors 18, which collect the radiation and bundle it in front of the applicator 13. The applicator contains a polarization filter. which is placed directly in front of the semiconductor diodes 17 and 17a, whereby the radiation can be better absorbed by the irradiated tissue.

According to FIGS. 2b and 2c the diodes 17 are placed in regular row arrangements, i.e., equidistant from each other, whereby, according to FIG. 2c, one applicator 13 additional to the diodes 17 has a light source 19. The diodes 17 radiate light in three wavelengths which are 600, 900 and 1200 nm, i.e., red and infrared (IR) radiation. The light source 19 formed as a cylinder as well as the diodes 17a (FIG. 2a) radiate light with a wavelength of 350–500 nm, i.e., blue light.

For the treatment of large-area tissues according to FIG. 1, more applicators 13 are connected and movable with respect to each other through hinges 10, respectively connecting one edge with the other, whereby the applicators are suitable for the treatment of, for example, the backs of humans and so become adjustable for an equidistant positioning of the applicators 13. The joint arm 12, shown at FIG. 3, connects one or more applicator(s) 13 with the standpillar 11. The jointed arm 12 has three joint carriers. 21, 22, 23, where the joint carrier 21, together with the standpillar 11 and the joint carrier 23 are moveable at a free end through a fixing joint 24 connected with one or more applicators 13. Another fixing joint 25 connects the joint carrier 23 with 21, while the joint carrier 22 is connected with the joint carrier 21 with a hinge 26. The joint carrier 21 is connected with the standpillar 11 through a joint 27. The jointed arm 12 thereby allows the positioning of the applicators 13 in front of, or above, a tissue area while maintaining a correct positioning distance. The jointed arm 12 also carries the electrical circuits 14 (not further described) from the control mechanism 16, which is integrated in standpillar 11, to the applicator(s) 13.

According to FIG. 4 the controller mechanism 16 consists of a generator 28, a timer 29, and a display 30. With help of the generator 28 the current impulses necessary to the production of light are contributed, while over timer 29, all time functions are adjustable, e.g. the duration of treatment. Display 30 shows pertinent treatment data, as current pulse frequency, pulse length and pulse amplitude. With help of the controller mechanism 16 the inventive device with reference to duration, amplitude and frequency of surge of current is adjustable within a relatively large range, so that the diodes 17, 17a and 19, as well as laser diodes with the same realization as diode 17, can be used as light sources. For that purpose the controller mechanism is equipped with a changeover switch for operating either with semiconductor diodes 17 or with laser diodes.

For the semiconductor diode mode, operating diodes 17 and at the same time the diodes 17a or 19 for blue light. are supplied with current pulse frequencies from 200 to 20,000 Hz with current pulse lengths between 2 and 200 microseconds. preferably between 2 and 20 microseconds, and current pulse amplitudes from 12 to 25 Volts. Operating this way overheating is avoided because of the short current pulse lengths. Therefore operation with a constant effect is attained. At the same time at each diode 17 produces simultaneous light emissions within the three separate wavelengths 600, 900 and 1200 nm. Through a simultaneous stimulation of the blue light diode's 17a, and 19, there are four radiation ranges with wavelengths of 350–500 nm (blue-light) as well as 600, 900 and 1200 nm which is available for therapeutic use. Light within the range of blue light stimulates activities within the cells and through that the regeneration of fatigued and sick tissue, especially the decomposition of fatty deposits during weight reduction therapy. The main radiation comes from the infrared semiconductor diodes 17. Radiation within the range of 600 nm stimulates primarily the vesicular respiration of the upper tissue, while the radiation within the range of 900 nm causes a stimulation of cells from the tissue surface down to about 70 mm in the deeper tissue. The radiation within the range of 1200 nm penetrates even deeper into the tissue and stimulates especially the water absorption in a living organism.

For the second operating mode, namely the laser operating mode, laser diodes work as light sources 17 supplied with current pulses with a frequency from 200 and 20,000 Hz, a current pulse length between 2 and 200 nanoseconds, preferably between 2 and 20 nanoseconds, and a current pulse amplitude from 40 to 400 Volts. A laser with a wavelength somewhere in the range from 400–1500 nm would have the same therapeutic effect as light of the same wavelength produced by semiconductor diodes 17, as long as the laser operating mode keeps the current pulse length for the photodynamic biostimulation within a range of 2–200 nanoseconds. Adjustment to short pulse lengths within the range of 2 to 20 nanoseconds combined with a high operating potential results in a double-photon radiation of the laser diode, which again causes a blue light radiation within the wavelength range of 350–500 nm. With the help of this two-photon tool in the right infrared range the relatively large energy of the blue light, which normally is already absorbed at the skin's surface, can be transmitted much deeper down into the tissue. During the absorption of the double photons (2.8 e.v.) cytochromes within the range of blue light are made active. Moreover the double photons stimulate the activity of the chymotrypsin enzymes.

The applicators 13, according to the FIGS. 2a. 2b and 2c, are equipped with sensors 32 arranged between the semiconductor or laser diodes 17. For therapeutic uses it is typically intended to apply a given amount of energy (Joule/ cm$^2$) per irradiated surface of tissue, which can be adjusted at the controller mechanism 16. Sensors 32 measure the amount of energy radiated away from the skin surface, which is indicative of the total energy penetrating into the tissue. Taking into account individual variations from patient to patient, the exposure can be determined according the measurements taken by sensors 32 so that the correct amount of therapeutic energy (Joule/cm$^2$) reaches the tissue.

An increase of the registered amount of energy can be achieved by the inventive device by increasing the operating potential (and thereby the pulse amplitude) or the pulse frequency and/or prolonging the duration of the treatment time through an adjustment of the controller mechanism 16.

While the applicators 13 according to FIGS. 2a. 2b and 2c are constructed for the treatment of larger tissue areas, the hand applicator's 15a. 15b according to FIGS. 5 and 8 are constructed for the treatment of small tissue areas.

The hand applicator 15a includes a cylindrical shaft 34 to which a headpiece 35 is connected. At the head piece 35 a printed circuit board 36 is fastened with light sources mainly from semiconductor diodes 17 (not described). At the printed circuit board 36 there can also be placed a blue light semiconductor diode 17a, which is stimulated in the same way as the diodes 1o of the applicators 13, so that light 38 of wavelengths 400, 600, 900 and 1200 nanometers is available, and according to FIG. 7, radiates from a cleft 37 in the head piece 35. For the polarization of the light rays, a polarization filter 41 is placed in front of the printed circuit board 36. The use of the polarization filter brings about the advantage that the radiation can be better absorbed by the treated tissue. The head piece 35 also has a radiation opening in the front 39. In headpiece 35, in front of the opening 39, are placed a lens for the focusing of the light rays 30 and a polarization filter 41, whereby as shown in FIG. 6 a light source (not described) radiates light 38 in an axial direction through lens 40 and polarization filter 41. The device with this kind of light 38 emission is especially designed for the treatment of small tissue areas, e.g. acupuncture points.

In the field of dermatology, light is used as a stand-alone therapy for wounds, leg ulcers, eczema, burns, etc., and as such is used to stimulate tissue directly. Light may also be used to treat tissue using photodynamic therapy (PDT) by activating chemical reactions in photosensitive chemicals introduced into or onto the tissue, such as photofrin, 5-aminolevulan acid, hermatoporphyrin, verteporfin, chlorins, phthalodyanines, phenothiazine, and benzoporphyrin-derivative monoacid-A (ATMPn) etc. for healing solar keratoses, basal cell carcinoma, melanomas, etc.

PDT substances may be administered in various forms: lotion or cream for topical application, tablets or capsules for oral injection, and local injection of solutions.

Dimethylsulfoxide (DMSO) is a solution which has the property of breaking down the barrier of the skin and is often used before administering PDT substances in order to increase the absorption thereof. Alternatively, PDT substances may be mixed with DMSO for application to the skin.

Treatment by light irradiation with the inventive device should not commence until sufficient absorption by the target tissue is obtained. Simply waiting for empirically determined times to elapse can suffice, or photodynamic diagnostic (PDD) may be employed to determine absorption. PDD comprises viewing the target area under illumination of a particular spectral content (such as from a fluorescent wood lamp) and observing apparent color of the target tissue.

High-intensity treatments (higher doses of PDT substances and strong irradiation) are used where it is desired to destroy tissue, as in destroying tumor tissue to cure cancer, or in hair removal where it is desired to destroy the hair follicle. Low-intensity treatments are used where it is desired to energize affected cells and to stimulate the local immune system, as in the rehabilitation of epicondylitis, tendonitis, arthritis, arthroses, gout, and pulmonary diseases; or in the treatment of acne, actinic keratoses, warts, onychomycosis, psoriasis, dermatitis, and basal carcinoma; and in improving the appearance of wrinkles, cellulite, and fat deposits.

Low-intensity treatments have been observed to activate aspects of the local immune system such as the macrophages, which produce prostaglandine E2 (PGE2) and TNF (pro-inflammatory zytokines. There have also been observed an accumulation of leucozytes in the venoles, and higher activity of the lymphozytes and plasma cells in the skin. The residual content TNF-α of proinflammatory zytokines has been detected in the urine of patients after having PDT treatment.

Treatment with the inventive device further enhances the efficacy of medicinal substances by photophoresis, a process of propelling fluids into the skin or tissue and propelling molecules through cell walls. The absorption process is speeded up, and amount of PDT substance absorbed is increased. Other methods of phoresis are in use, such as galvanic-iono-phoresis, exchange phoresis, and phonophoresis. These methods create a concentration gradient across the skin, and a resultant Brownian molecular motion creates a thermal influence which enhances transfer of medicaments. However, this warming may be uncomfortable, and may render impossible a facelift using a collagen facemask, since collagen will not withstand temperatures above 27 degrees Celsius.

Photofrin is PDT substance which is administered by injection, at a dosage of 1–2 mg. per kg. of the patient's weight. 48 hours is allowed for absorption of the photofrin by the tissue to be treated, during which time the patient is kept in dim light. The treatment consists of irradiation by the inventive device. The patient remains photosensitive for 6 to 8 weeks, and should avoid strong light and direct sunlight during that time.

ALA (5-Aminolavulinacid) is externally applied as a 10 to 20 percent mixture in an oil in water emulsion or in a cream. 4 to 6 hours is allowed for absorption, during which time the patient should remain in dim light. After treatment by irradiation from the inventive device, the patient remains photosensitive for 24 to 48 hours, during which he should avoid strong light and direct sunlight.

L-Phenylalanin is applied in liquid form as a lotion or a spray or in a cream form, in a 5 to 30 percent mixture according the severity of the condition to be treated. Optical irradiation with the inventive device may begin almost immediately. Alternatively, doses of 50 to 100 mg. may be taken orally 30 to 60 minutes before irradiation. The patient is photosensitive for 24 hours after application.

Ammi visnaga is an herbal substance obtained from a dried extract of the fruit ammeos visnagae fructus. Its molecular structure is depicted in FIG. 10. Fluid application of a 5 to 30 percent mixture (according to pathology) in the form of a lotion, spray, or cream is performed shortly (30 minutes) before irradiation, or an oral dose of 100 mg. is given 2 to 3 hours before irradiation. The patient need not be kept in a darkened room before irradiation, and may be subjected to normal incidence of direct sunlight immediately after treatment although he should avoid outright sunbathing and basking for several days.

Tests indicate that ammi visnaga solution prepared in the homeopathic manner is effective at lower concentrations, which is advantageous both from the standpoint of economics (the ammi visnaga extract may cost several dollars per gram) and because of a lowered risk of toxicity (side effects). In a homeopathic preparation, the herb is first micronized and a weak solution in a fluid medium such as alcohol, sterile water, or oil (glycerine) is prepared and bottled. Vibrations are introduced into it by concussing the bottle repetitively against a medium-hard surface such as a rubber plate on a table, or by subjecting the bottle to low-frequency (1 to 500 Hz.) electromagnetic vibrations, which pulls energy out of the micronized herb into the entire solution. The solution must be prepared so that the molecule size is comparable to that for amino acids, so that the molecules may easily permeate cell membranes.

PDT has been used successfully in the treatment of internal inoperable cancers. A biopharmaceutical (specifically, hermatoporphyrin) is injected into the tumor tissue, and an optical method known as photodynamic diagnostic (PDD) is used to determine when the biopharmaceutical has been absorbed by the entire tumor. Then the tumor tissue is irradiated with light typical for a dye laser, which activates the photosensitive reactors in the hermatoporphyrin, whereby singlet oxygen is liberated. Singlet oxygen is toxic to protein and phosphorlipids in the tumor tissue, whereby the tumor is destroyed without destroying the surrounding tissue.

For treatment of skin keratosis (precancerous tissue), trials with, for example, 5-aminolevulinic acid have shown that it can be used effectively in PDT if introduced into oil in a water suspension which is then applied to skin keratosis and then irradiated with a light source. A fast and cosmetically perfect healing has been attained with a very low rate of recurrence compared to conventional treatments, such as cryotherapy.

Common dermatological diseases like acne, warts, and onychomycosis (nail fungus) can be successfully and effectively treated using PDT (with ALA/5-aminolevulanic acid) at a lower concentration than has conventionally been used. The treatment works not by causing cell death as light treatment has historically done, but instead works by stimulating the immune system so as to enable it to better control the inflammatory reaction to oil gland activity. The irradiation at multiple wavelengths as provided by the present invention enhances the efficacy of treatment in this manner.

Stimulating the immune system so as to reduce inflammatory reactions has also been found effective in the therapy of many other conditions, for example, epicondylitis (tennis elbow), tendonitis, gout, arthritis, arthroses, pulmonary diseases, and numerous other muscular and joint symptoms. Good results have been obtained with PDT in conjunction with the present invention's multiple wavelength output. Studies indicate that the patient often is pain-free after only one treatment, and the number of treatments can be reduced to 3–4, instead of 12–20 as required without the inventive device.

The PDT substance is applied topically as cream or oil in water suspension, typically a 10–15 percent solution. Augmented action may be obtained by use of injection instead of or in addition to topical application. A large joint such as the knee requires 10–12 subcutaneous or intra-muscular injections, preferably at the trigger points, while for a smaller joint such as the elbow 5–6 injections is sufficient. First the trigger points are found and irradiated for 30 seconds with hand applicator of the present invention. This gives an anesthetic effect, which is useful for lessening discomfort from the injections. (Injection at the trigger points is known for reduction of pain.) Then, after determination that the PDT substance is absorbed by the target tissue, the surface applicator of the present invention is folded around the target joint and irradiation takes place for 30 minutes. Ammi visnaga can be selected as a homeopathic PDT solution both for topical use and for the trigger-point injections.

Good results have also been obtained in the physiotherapy and physical rehabilitation with the present invention's ability to radiate visible light in conjunction with several wavelengths of infrared light which is able to penetrate to deep tissue.

FIG. 8, in connection with FIG. 9, describes a hand applicator 15b, which is especially intended for dental treatment. The applicator 15b shows at the front end of the shaft 42 a printed circuit board 43, where an IR semiconductor diode (IR infrared light) 44 and a semiconductor diode (blue light) 45 are placed, where the diode 44 is stimulated to radiate light with the described three wavelengths and the diode 45 is stimulated to radiate the described wavelength range of 350–500 nm. In front of the printed circuit board 43 a head piece 46 is placed, connected with a fastened hollow expander 47, in which an optical fiber is sealed (not shown). The head piece 46 is in front of the printed circuit board 43 so it can be rotated 180°, so that the expander 47 can be positioned in front of either the diodes 44 or 45. If the expander 47 is positioned, for example, in front of the diode 44, light with the wavelengths 600, 900 and 1200 nanometer is transmitted through the optical fiber in expander 47 and ultimately strikes the tissue, e.g. gum tissue, through which painful gingival diseases can be eliminated. Through a positioning of the expander 47 in front of the blue light semiconductor diode 45, blue light is conducted through the expander 47, with which plastic fillings in teeth can be hardened. It is obvious that the light rays with this form of execution can also be conducted through polarization fibers. Furthermore, the two hand applicators are equipped with sensors 32 for the same purpose as described for the applicators 13.

The control unit of the present invention causes output of the blue light to be at 25% of full output for the first ten seconds, and full power thereafter. This results in better hardening of the fillings, without shrinkage.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A device for photodynamic stimulation of human cells, comprising:
   a base housing containing a control mechanism and a pulse generator; and
   at least one applicator equipped with at least one pulsed first light source connected to said pulse generator; wherein:
   the generator is configured to selectably supply electrical pulses at a frequency between 200 and 20,000 Liz., a pulse length between 2 and 200 microseconds, and an amplitude of between 2 and 25 volts;
   the at least one first light source is a semiconductor diode which emits light of approximately 600, 900, and 1200 nanometers in response to said pulses from said generator; and
   wherein the at least one applicator comprises sensors connected to the control mechanism for measurement of reflected light for feedback control and automatic adjustment.

2. A device according to claim 1, wherein at least one of the first light sources is a semiconductor diode which emits blue-light radiation in the range of 350 to 500 nanometers.

3. A device according to claim 1, wherein at least one of the first light sources is a tube which emits blue-light radiation in the range of 350 to 500 nanometers.

4. A device according to claim 1, wherein the at least one applicator is mounted to the base housing by means of a movable-joint arm.

5. A device according to claim 4, wherein the at least one applicator comprises several single applicators hinged together so as to be adjustable at angles with respect to one another.

6. A device according to claim 1, further comprising a hand-held applicator comprising at least one second light source connected to said pulse generator and at least one light outlet.

7. A device according claim 6 wherein the hand-held applicator is equipped with a shaft and a head and a printed circuit board equipped with semiconductor diodes.

8. A device according to claim 7 wherein:
   at least a first semiconductor diode on the printed circuit board radiates red and infrared light at wavelengths of approximately 600, 900, and 1200 nanometers;
   at least a second semiconductor diode on the printed circuit board radiates blue light in the range of approximately 350 to 500 nanometers;
   the head comprises an expander rotatable to selectably conduct blue light or red and infrared light to said at least one light outlet.

9. A device according to claim 8, wherein the expander includes a fiber optic cable.

10. A device according to claim 8, wherein the light output is at approximately 25% of a selected level for approximately 10 seconds and is at the selected level thereafter.

11. A device according to claim 6 wherein the at least one light outlet is equipped with a mounted lens.

12. An apparatus according to claim 1, wherein the pulse duration is limited to 20 microseconds.

13. A method of treating tissue, comprising the steps of:
   introducing a photosensitive substance to the tissue;
   determining when the tissue has absorbed a predetermined level of the photosensitive substance; and
   irradiating the tissue with a device according to claim 1.

14. A method according to claim 13, wherein the step of introducing a photosensitive substance to the tissue comprises topical application of a lotion containing the photosensitive substance.

15. A method according to claim 13, wherein the step of introducing a photosensitive substance to the tissue comprises oral ingestion of a substance comprising at least the photosensitive substance.

16. A method according to claim 13, wherein the step of introducing a photosensitive substance to the tissue comprises subcutaneous injection of a substance comprising at least the photosensitive substance.

17. A method according to claim 13, wherein the photosensitive substance is one of photofrin, 5-aminolevulan acid, hermatoporphyrin, verteporfin, chlorins, phthaldodyanines, phenothiazine, benzoporpliyrin-derivative monoacid-A (AT-MPn), L-Phenylalanin, and ammi visnaga.

18. A method according to claim 13, wherein dimethylsulfoxide is also introduced to the tissue.

19. A method according to claim 13, wherein dimethylsulfoxide is mixed with the photodynamic substance.

20. A method according to claim 13, wherein:
   the photosensitive substance is photofrin;
   the photosensitive substance is introduced to the tissue of a patient by subcutaneous injection of 1 to 2 mg. per kg. of the patient's weight;
   the patient is kept in dim light for approximately 48 hours before irradiation; and
   the patient is kept out of strong light for approximately eight weeks after irradiation.

21. A method according to claim 13, wherein:
   the photosensitive substance is 5-Aminolavulin acid;
   the photosensitive substance is introduced to the tissue of a patient by topical application of a 10 to 20 percent mixture in one of an oil-in-water emulsion and a cream;
   the patient is kept in dim light for approximately six hours before irradiation; and
   the patient is kept out of strong light for approximately 48 hours after irradiation.

22. A method according to claim 13, wherein:
   the photosensitive substance is L-Phenylalanin;
   the photosensitive substance is introduced to the tissue of a patient by topical application of a 5 to 30 percent mixture according to a degree of treatment desired; and
   the patient is kept out of strong light for approximately 24 hours after application.

23. A method according to claim 13, wherein:
   the photosensitive substance is L-Phenylalanin;
   the photosensitive substance is introduced to the tissue of a patient by oral ingestion of 50 to 100 mg according to the patient's weight and to degree of treatment desired;
   the patient is kept in dim light for approximately 60 minutes before irradiation; and
   the patient is kept out of strong light for approximately 24 hours after application.

24. A method according to claim 13, wherein:
   the photosensitive substance is amxni visnaga;
   the photosensitive substance is administered to the tissue of a patient by topical application of a 5 to 30 percent mixture, according to degree of treatment desired, in a liquid medium;
   the patient avoids direct sunlight for approximately 30 minutes before irradiation; and
   the patient avoids sunbathing for approximately five days after irradiation.

25. A method according to claim 13, wherein:
the photosensitive substance is ammi visnaga;
the photosensitive substance is administered to the tissue of a patient by oral ingestion of approximately 100 mg. thereof;
the patient avoids direct sunlight for approximately three hours before irradiation; and
the patient avoids sunbathing for approximately five days after irradiation.

26. A method according to claim 13, wherein the step of determining when the tissue has absorbed a predetermined level of the photosensitive substance comprises observing that the tissue undergoes a predetermined color change when viewed under a predetermined illumination.

27. A method according to claim 26, wherein the predetermined illumination comprises a wood lamp.

28. A method according to claim 13, wherein the pulse duration is limited to 20 microseconds.

29. A device for photodynamic stimulation of human cells, comprising:
a base housing containing a control mechanism and a pulse generator; and
at least one applicator equipped with at least one pulsed first light source connected to said pulse generator;
wherein:
the generator is configured to selectably supply electrical pulses at a frequency between 200 and 20,000 Hz., a pulse length between 2 and 200 nanoseconds, and an amplitude of between 40 and 400 volts;
the at least one first light source is a laser diode which emits light of approximately 600, 900, and 1200 nanometers in response to said pulses from said generator; and
wherein the at least one applicator comprises sensors connected to the control mechanism for measurement of reflected light for feedback control and automatic adjustment.

30. A device according to claim 29, wherein at least one of the first light sources is a laser diode which emits blue-light radiation in the range of 350 to 500 nanometers.

31. A device according to claim 29, wherein at least one of the first light sources is a tube which emits blue-light radiation in the range of 350 to 500 nanometers.

32. A device according to claim 29, wherein the at least one applicator is mounted to the base housing by means of a movable-joint arm.

33. A device according to claim 32, wherein the at least one applicator comprises several single applicators hinged together so as to be adjustable at angles with respect to one another.

34. A device according to claim 29, further comprising a hand-held applicator comprising at least one second light source connected to said pulse generator and at least one light outlet.

35. A device according claim 34 wherein the hand-held applicator is equipped with a shaft and a head and a printed circuit board equipped with laser diodes.

36. A device according to claim 35 wherein:
at least a first laser diode on the printed circuit board radiates red and infrared light at wavelengths of approximately 600, 900, and 1200 nanometers;
at least a second laser diode on the printed circuit board radiates blue light in the range of approximately 350 to 500 nanometers;
the head comprises an expander rotatable to selectably conduct blue light or red and infrared light to said at least one light outlet.

37. A device according to claim 36, wherein the expander includes a fiber optic cable.

38. A device according to claim 36, wherein the light output is at approximately 25% of a selected level for approximately 10 seconds and is at the selected level thereafter.

39. A device according to claim 34 wherein the at least one light outlet is equipped with a mounted lens.

40. An apparatus according to claim 29, wherein the pulse duration is limited to 20 nanoseconds.

41. A method of treating tissue, comprising the steps of:
introducing a photosensitive substance to the tissue;
determining when the tissue has absorbed a predetermined level of the photosensitive substance; and
irradiating the tissue with a device according to claim 29.

42. A method according to claim 41, wherein the step of introducing a photosensitive substance to the tissue comprises topical application of a lotion containing the photosensitive substance.

43. A method according to claim 41, wherein the step of introducing a photosensitive substance to the tissue comprises oral ingestion of a substance comprising at least the photosensitive substance.

44. A method according to claim 41, wherein the step of introducing a photosensitive substance to the tissue comprises subcutaneous injection of a substance comprising at least the photosensitive substance.

45. A method according to claim 41, wherein the photosensitive substance is one of photofrin, 5-aminolevulan acid, hermatoporphyrin, verteporfin, chlorins, phthaldodyanines, phenothiazine, benzoporphyrin-derivative monoacid-A (AT-MPn), L-Phenylalanin, and ammi visnaga.

46. A method according to claim 41, wherein dimethylsulfoxide is also introduced to the tissue.

47. A method according to claim 41, wherein dimethylsulfoxide is mixed with the photodynamic substance.

48. A method according to claim 41, wherein:
the photosensitive substance is photofrin;
the photosensitive substance is introduced to the tissue of a patient by subcutaneous injection of 1 to 2 mg. per kg. of the patient's weight;
the patient is kept in dim light for approximately 48 hours before irradiation; and
the patient is kept out of strong light for approximately eight weeks after irradiation.

49. A method according to claim 41, wherein:
the photosensitive substance is 5-Aminolavulin acid;
the photosensitive substance is introduced to the tissue of a patient by topical application of a 10 to 20 percent mixture in one of an oil-in-water emulsion and a cream;
the patient is kept in dim light for approximately six hours before irradiation; and
the patient is kept out of strong light for approximately 48 hours after irradiation.

50. A method according to claim 41, wherein:
the photosensitive substance is L-Phenylalanin;
the photosensitive substance is introduced to the tissue of a patient by topical application of a S to 30 percent mixture according to a degree of treatment desired; and
the patient is kept out of strong light for approximately 24 hours after application.

51. A method according to claim 41, wherein:
the photosensitive substance is L-Phenylalanin;
the photosensitive substance is introduced to the tissue of a patient by oral ingestion of 50 to 100 mg according to the patient's weight and to degree of treatment desired;

the patient is kept in dim light for approximately 60 minutes before irradiation; and the patient is kept out of strong light for approximately 24 hours after application.

52. A method according to claim 41, wherein:

the photosensitive substance is ammi visnaga;

the photosensitive substance is administered to the tissue of a patient by topical application of a 5 to 30 percent mixture, according to degree of treatment desired, in a liquid medium;

the patient avoids direct sunlight for approximately 29 minutes before irradiation; and the patient avoids sunbathing for approximately five days after irradiation.

53. A method according to claim 41, wherein:

the photosensitive substance is ammi visnaga;

the photosensitive substance is administered to the tissue of a patient by oral ingestion of approximately 100 mg. thereof;

the patient avoids direct sunlight for approximately three hours before irradiation; and the patient avoids sunbathing for approximately five days after irradiation.

54. A method according to claim 41, wherein the step of determining when the tissue has absorbed a predetermined level of the photosensitive substance comprises observing that the tissue undergoes a predetermined color change when viewed under a predetermined illumination.

55. A method according to claim 54, wherein the predetermined illumination comprises a wood lamp.

56. A method according to claim 41, wherein the pulse duration is limited to 20 nanoseconds.

* * * * *